United States Patent

Nilsson et al.

[11] Patent Number: 5,472,671
[45] Date of Patent: * Dec. 5, 1995

[54] CUVETTE

[76] Inventors: Sven-Erik Nilsson, Döbeliusvägen 39; Jan Lilja, Södra Brunnsvägen 63, both of SE-256 54 Helsingborg, Sweden

[*] Notice: The portion of the term of this patent subsequent to Feb. 15, 2011, has been disclaimed.

[21] Appl. No.: 196,640

[22] Filed: Feb. 14, 1994

Related U.S. Application Data

[63] Continuation-in-part of Ser. No. 768,321, Oct. 17, 1991, Pat. No. 5,286,454.

[30] Foreign Application Priority Data

Apr. 26, 1989 [SE] Sweden .................................. 8901518

[51] Int. Cl.$^6$ ...................................................... B01L 3/00
[52] U.S. Cl. ............................ 422/102; 422/101; 422/72; 422/57; 422/58; 436/177; 436/178
[58] Field of Search .................................. 422/57, 58, 61, 422/72, 101, 102, 56; 436/164, 63, 177–178, 180, 70, 69; 356/246

[56] References Cited

U.S. PATENT DOCUMENTS

| | | | |
|---|---|---|---|
| 3,799,742 | 3/1974 | Coleman | 422/102 |
| 4,088,448 | 5/1978 | Lilja et al. | 422/58 |
| 4,462,964 | 7/1984 | Guigan | 422/72 |
| 4,654,197 | 3/1987 | Lilja et al. | 422/58 |
| 4,714,590 | 12/1987 | Guigan | 422/102 |
| 4,734,262 | 3/1988 | Bagshawe | 422/102 |
| 4,806,316 | 2/1989 | Johnson et al. | 422/58 |
| 4,963,498 | 10/1990 | Hillman et al. | 422/102 |
| 5,286,454 | 2/1994 | Nilsson et al. | 422/102 |

Primary Examiner—Robert J. Warden
Assistant Examiner—Hien Tran
Attorney, Agent, or Firm—Kane, Dalsimer, Sullivan et al.

[57] ABSTRACT

The present invention is a cuvette provided with at least two cavities. The first or inlet cavity takes up fluid by capillary action. The second cavity is a reception cavity which communicates with the first cavity through a first channel. The second cavity preferably is constructed and arranged to not exert a capillary action, although it could be constructed to exert a capillary action. The first channel which is in fluid communication with the first cavity and the second cavity exerts a non-capillary and non-spontaneous fluid transporting function that is operative only under an external influence, such as by application of a centrifugal force on the cuvette. The cuvette is well suited for a variety of analyses, particularly upon whole blood.

8 Claims, 2 Drawing Sheets

CUVETTE

This is a continuation-in part of application(s) Ser. No. 07/768,321 filed on Oct. 17, 1991, now U.S. Pat. No. 5,286,454.

FIELD OF THE INVENTION

The present invention is directed to a cuvette for taking up fluid and mixing the fluid with a reagent for analyzing the mixture. The cuvette has at least one cavity in which the fluid can be taken up through an inlet.

BACKGROUND OF THE INVENTION

A cuvette used for direct optical analysis of a fluid mixture is disclosed in U.S. Pat. No. 4,088,448. The cuvette according to this patent consists of a body having two flat surfaces spaced a predetermined distance from each other thereby forming an optical path and defining a cavity. The cavity has an inlet through which it communicates with the ambient atmosphere. The cavity has a predetermined fixed volume, and the predetermined distance between the surfaces enables the cavity to take up a sample by capillary action. Further, a reagent is applied to the surfaces of the cavity.

This cuvette offers many advantages over prior art apparatuses of this kind. A fluid can be taken up into the cuvette for mixing and chemical reaction with a suitable reagent, e.g. for color development in the same cavity used for a subsequent measuring operation. Thus, the cuvette disclosed in U.S. Pat. No. 4,088,448 simplifies the sampling procedure, reduces the amount of accessory equipment, and in most cases—depending on the type of analysis—considerably increases the accuracy of the analysis since the analysis procedure is independent of the level of skill of those carrying out the analysis.

U.S. Pat. No. 4,654,197 discloses a cuvette which by using a semipermeable membrane as part of the cuvette, increases the number of reactions possible in the cuvette system.

U.S. application Ser. No. 768,321, filed Oct. 17, 1991, now U.S. Pat. No. 5,286,454 discloses a cuvette for taking up at least one fluid and for mixing a fluid with a dry reagent for analyzing a mixture, wherein the cuvette comprises:

a) at least one capillary first cavity having an inlet and constructed and arranged to take up a fluid in capillary action alone;

b) a first channel having a non-capillary and non-spontaneous fluid transporting function operative only under external influence by application of a centrifugal force on the cuvette;

c) a centrifugation reception cavity communicating with the at least one capillary first cavity via the first channel and constructed and arranged to exert no capillary action;

d) at least one capillary second cavity constructed and arranged to take up a fluid by capillary force alone; and e) a first capillary transporting means projecting into the centrifugation reception cavity, being connected to the at least one capillary second cavity and constructed and arranged to transport fluid by capillary action from the centrifugal reception cavity into the at least one capillary second cavity. The centrifugation reception cavity can be divided into two sections: a first, lower section for receiving heavy material for taking up the fluid, and a second, upper section which serves as a measuring cavity.

Instead of relying on centrifugal force for fluid transport through the channel, it is possible to exert a pressure on the fluid in the first cavity. In this case a venting device is necessary. The walls of the various channels, or desired portions thereof, may be coated with reagent, and an analysis can be carried out on fluid in both the first cavity and the second or the capillary section of the reception cavity, and also in the heavier-material section of the reception cavity.

From U.S. Pat. Nos. 4,462,964 and 4,714,590 it is known to provide capillary orifices in the fluid path of a cuvette used of analyses. Contrary to the arrangement of the present invention, these orifices serve to prevent fluid transport until the cuvette is subjected to centrifugation.

SUMMARY OF THE INVENTION

In the preferred embodiment, the new cuvette is provided with at least two cavities. The first or inlet cavity provides means for taking up fluid by capillary action. The second cavity is a reception cavity which communicates with the first cavity by means of a first channel. The second cavity preferably is constructed and arranged to not exert a capillary action, although it could be constructed to exert a capillary action.

The first channel which is in fluid communication with the first cavity and the second cavity exerts a non-capillary and non-spontaneous fluid transporting function that is operative only under an external influence, such as by application of a centrifugal force on the cuvette. The present invention also embraces other embodiments based upon the principles delineated above.

One advantage of the improved cuvette according to the invention is that even though an analysis must be performed on plasma or serum, the sample may still be whole blood. Thus, the cuvette can be used for analysis within a much broader range than the cuvettes according to U.S. Pat. No. 4,088,448 and 4,654,197. Another major advantage over prior art cuvettes is that the use of the centrifugal force makes it possible to carry out different reactions in different cavities, thus allowing a period of incubation before the next reagent is used. Yet another advantage is that material produced or used in a reaction, such as precipitated proteins or immunoaggregates, which might otherwise interfere with subsequent reactions or measurements, can be separated by centrifugation.

The cuvette can be manufactured from glass or polymeric material. It is also possible to manufacture from many other materials, e.g. different types of semi-permeable materials, such as those used in the cuvette according to U.S. Pat. No. 4,654,197, or optically transparent or non-transparent materials. The reagent, which is provided in at least one cavity, can be deposited by evaporation, freeze-drying, spraying, screen-printing or by other techniques.

The functional parts of the cuvette may vary depending on the fluid to be analyzed and the type of analysis. For the inlet cavity to take up the fluid by capillary action, the distance between the cuvette walls must be less than 1 mm, and preferably less than 0.7 mm. If this is not the case, the capillary action must be brought about by means other than the walls, and the wall material must be wettable with the fluid or treated to be so.

The volume of the inlet cavity depends on the effective amount of fluid necessary for the succeeding cavities and the amount of material to be separated by centrifugation. The channel connecting the first cavity to the second or the reception cavity has low capillary action, that is, the distance between the walls exceeds 0.7 mm. The walls defining the channel may suitably be manufactured from non-wettable material or treated so as to be non-wettable. The channel may contain non-wettable filtering material or other means for preventing spontaneous transport of fluid from the first cavity. Due to this arrangement, the amount of fluid taken up is fairly exact and can be set during the manufacture of the cuvette. By a suitable design of the channel, it can also be used for mixing the fluid passing through it during the centrifugation and, as indicated above, may also be provided with a reagent.

The invention will be described in more detail below, with reference to the accompanying drawings schematically illustrating some embodiments.

DETAILED DESCRIPTION OF THE EMBODIMENTS

Figure 1:
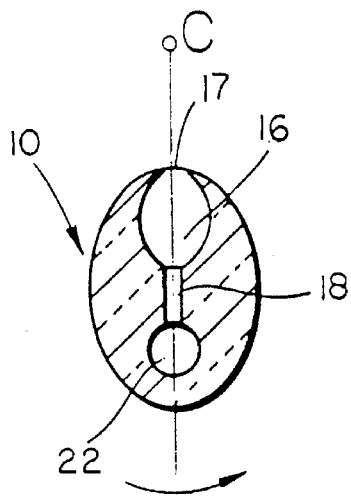
FIG. 1 depicts the preferred embodiment of the present invention.
Figure 2:
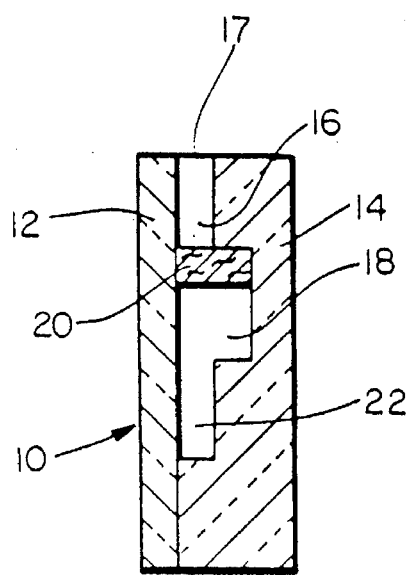
FIG. 2 is a second view of the preferred embodiment of the present invention.

Referring to FIGS. 1 and 2, cuvette 10 is provided with first and second walls 12 and 14, respectively, which are constructed of glass or polymeric material. The walls 12 and 14 may also comprise other materials and items such as optical windows, semipermeable membranes, and electrode materials to name a few alternatives. The walls 12 and 14 define a plurality of areas having different depths. A first cavity 16 serves as an inlet cavity. The first cavity 16 is constructed to be of a depth which facilitates the taking up of liquid by capillary action. First cavity 16 is provided with capillary inlet 17 which communicates with the ambient atmosphere and through which the liquid sample is drawn.

The first cavity 16 may be provided with a reagent which reacts with the liquid sample drawn into the cavity. The reagent may be deposited on the walls of the cavity by evaporation, freeze drying, spraying, screen printing or other known means. The first cavity may also contain a reagent for modifying the sample.

The first cavity 16 is in fluid communication with first channel 18, which exhibits a non-capillary and non-spontaneous fluid transporting function. To cause fluid flow through first channel 18 an external force, preferably centrifugal force, must be exerted. The first channel 18 is constructed to be of a depth so that fluid will not flow therethrough in a capillary or spontaneous manner. In FIG. 2, it can be seen that first channel 18 is of a depth substantially greater than first cavity 16, which draws fluid by capillary action.

In addition to exhibiting non capillary and non-spontaneous fluid transporting function by virtue of its depth, first channel 18 may be provided with a coating of hydrophobic material, or the walls of the first channel 18 may be constructed of such a material. The first channel may also be provided of a hydrophobic filtering material 20. First channel 18 may also be provided with a reagent or modifying agent.

First channel 18 is in turn in fluid communication with reception cavity 22. When a centrifugal force is applied to the cuvette of the present invention, the external force causes fluid to flow through the first channel 18 and enter the reception cavity 22.

Figure 7:
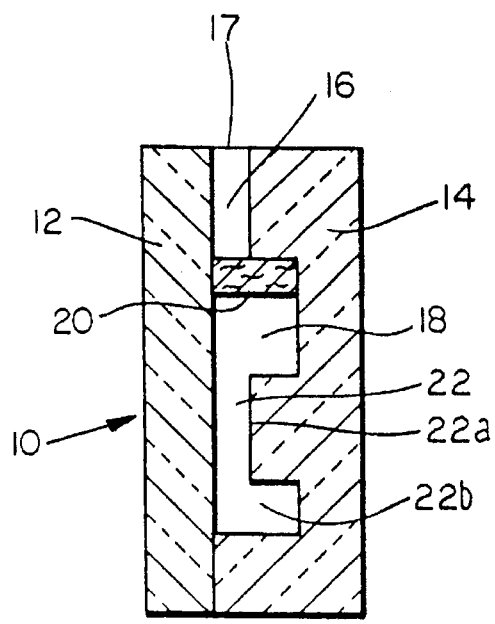
FIG. 7 depicts a modification of the preferred embodiment.

Reception cavity 22 is preferably constructed of two sections 22a and 22b (FIG. 7). Where two sections are provided the volume of the first cavity 16 is equal to or slightly greater than the volume of both sections 22a and 22b in order to insure that upper section fills 22a entirely on centrifugation. Lower section 22b serves as a sediment chamber for heavier materials in the original fluid. The upper section 22a serves as the measuring area for the particular test that is being run, and where separation of fluid components is necessary it is the area of the reception cavity which is provided with reagent. During centrifugation, heavier material will settle in lower section 22b, and fluid will remain in the upper section 22a, or measuring area. The upper section 22a could be constructed to exert a capillary function to prevent fluid from returning to first channel 18 after centrifugation.

The cuvette can be used as follows. The first cavity 16 is filled with a liquid sample which is drawn into the cavity 16 through capillary inlet 17. The liquid sample mixes with the reagent or other agent, if provided in the cavity, so that the mixture can be analyzed by a photometer or other analytical device.

Upon subjecting the cuvette to an external force, such as centrifugal force, the liquid sample or a portion thereof forced through the first channel 18 which exhibits non-capillary or non-spontaneous fluid flow properties and then enters the reception cavity 22. To effect fluid movement as described herein, it should be understood that the center of rotation (C in FIG. 1) should be located in such a way that the fluid is forced towards reception cavity 22 and not towards inlet 17. Preferably, the center of rotation C is located on the extension of a line interconnecting first cavity 16 and reception cavity 22.

It is possible than an optical analysis can be performed both on fluid when it is in the first cavity 16 and on the fluid in the reception cavity 22 after centrifugation. As an example, an optical hemoglobin-measurement can be performed in the first cavity 16 as a first analysis before centrifugation takes place. Upon centrifugation of the cuvette an optical glucose-measurement can be performed on the fluid in the reception cavity 22.

Figure 6:
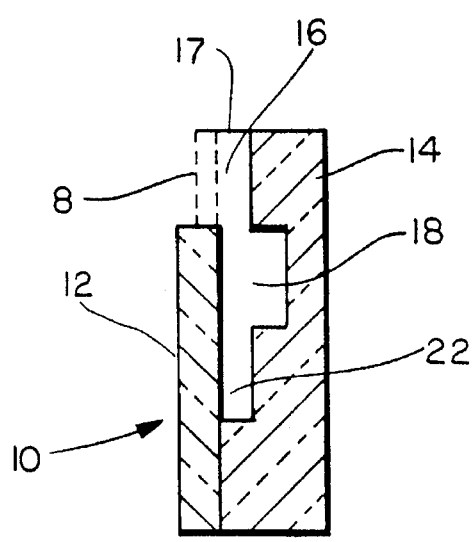
FIG. 6 depicts a fifth embodiment of the present invention.

FIG. 6 shows another variation on the embodiment shown in FIG. 1. In this embodiment, a portion of the wall 12 defining the cavity 16 has been replaced with a semipermeable membrane 8, as in U.S. Pat. No. 4,654,197.

Figure 3:
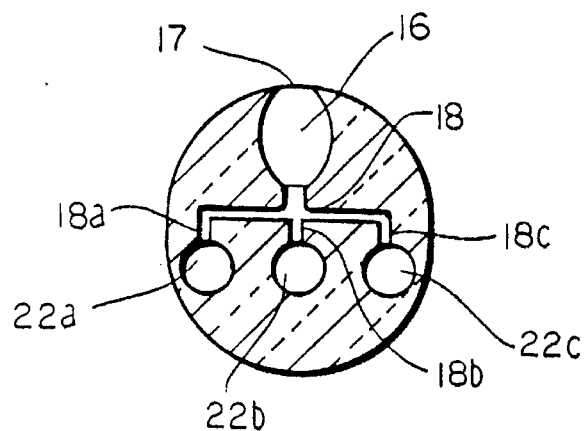
FIG. 3 depicts a second embodiment of the present invention.

FIG. 3 shows another embodiment of the present invention. First cavity 16 and capillary inlet are provided as previously described. However the first channel 18 having a non-capillary and non-spontaneous fluid transporting function is branched (18a, 18b, 18c) to communicate with a plurality of reception cavities 22a, 22b and 22c which are arranged in parallel. The first channel 18 may be provided with hydrophobic filters, coatings, or construction, or may be coated with reagent as set forth previously. Reception cavities 22a, 22b, and 22c may be provided with reagents or modifying agents as set forth previously.

Figure 4:
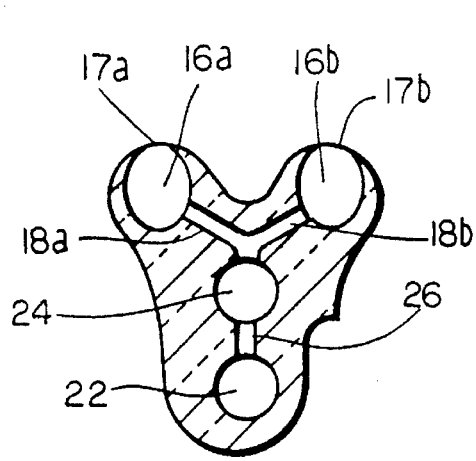
FIG. 4 depicts a third embodiment of the present invention.

FIG. 4 depicts an embodiment adapted for the situation where the user of the cuvette needs freedom to choose the diluent or reagent to be mixed with the reaction fluid. The reaction fluid or first fluid is drawn into the first cavity 16a through inlet 17a. Second cavity 16b is provided with inlet 17b and exerts capillary action, as it is constructed in the same manner as first cavity 16a. A second fluid, such as a reagent or diluent can be drawn into second cavity 16b through capillary action inlet 17b.

First cavity 16a and second cavity 16b are in fluid communication with first channels 18a and 18b which exert a non-capillary and non-spontaneous fluid transporting function. First channels 18a and 18b are in fluid communication with mixing cavity 24, which provides a place for in situ mixing effected by centrifugation of the first and second fluids. The mixing cavity 24 is in fluid communication with a second channel 26, which exerts a non-capillary and non-spontaneous fluid transporting function and which in turn is in fluid communication with the reception cavity 22.

In operation, the first fluid is drawn into the cavity 16a by capillary action through inlet 17a. Likewise a second fluid, which is a reagent or the like, is drawn into second channel 16b by capillary action through inlet 17b. By subjecting the cuvette to an external force, such as centrifugal force, the first and second fluids will flow through first channels 18a and 18b into centrifugal mixing cavity 24, where the first and second fluids are mixed. Further, the centrifugal force will cause fluid to flow through the second channel 26 into reception cavity 22. Reception cavity 22 may be provided with two sections 22a and 22b as shown in FIG. 7. The second channel 26 may be branched as in FIG. 3 and connected to a plurality of reception cavities.

First channels 18a and 18b, mixing cavity 24, second channel 26, and reception cavity 22 may be constructed and provided for with reagents, other agents, and as previously set forth herein.

Figure 5:
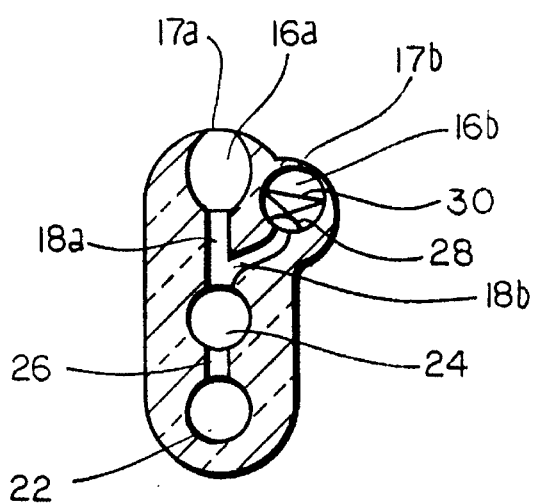
FIG. 5 depicts a fourth embodiment of the present invention.

FIG. 5 depicts an embodiment similar to that of the embodiment of FIG. 4. However, the embodiment of FIG. 5 is provided in the second cavity 16b with a seal 28 which effectively encloses a fluid within the second cavity and initially prohibits fluid communication between second cavity 16b and first channel 18b. The second cavity 16b is also provided with a perforating means 30 which is positioned to rupture the seal 28 is constructed to rupture upon centrifugation. The centrifugal force urges the perforating means 30 against the seal 28 and into engagement therewith so as to penetrate the seal, thereby permitting fluid flow from second cavity 16b into first channel 18b.

EXAMPLE 1

Determination of hemoglobin and glucose in whole blood

A red blood cell, also known as an erythrocyte, carry inside its semipermeable membrane, a plurality of water-soluble high and low molecular weight chemical substances, such as hemoglobin (high-molecular weight) and glucose (low-molecular weight). Low-molecular weight substances exist both intra-cellularly and extracellularly, whereas high-molecular weight substances usually cannot pass through the membrane of the erythrocyte. When determining the glucose or hemoglobin content of whole blood the semi-permeable membrane of the erythrocyte is ruptured by means of a detergent, an osmotic shock, or a combination thereof. This renders the substances contained in the erythrocytes available for chemical analysis.

Hemoglobin

In a cuvette according to FIGS. 1 and 2, the cavity 16 is supplied with a dry chemical reagent consisting of 0.30 mg sodium deoxycholate;

0.15 mg sodium azide;

0.15 mg sodium nitrite; and 0.1 mg non-reactive ingredients.

The reagent composition for a certain cuvette is dissolved in a small amount of water and Pluronic P85®. The reagent composition has a viscous consistency so that it can be uniformly applied over the surface in the cavity 16, such as by screen-printing or dabber printing.

The cuvette of this embodiment is well suited for use with whole blood. When combined with hemoglobin, the reagent composition produces a hemoglobin-azide complex which can be determined photometrically in the reception cavity 22. The reagent dissolves into the blood, and the chemical reaction forming the hemoglobin-azide complex is completed after about 45 seconds. The contents in the cavity 16 are transferred through first channel 18 by centrifugal force into the reception cavity 32, where a clear, low-turbid solution can be analyzed by photometry. The distance between the walls in the cavity 21 is about 0.13 min.

Glucose

The cuvette of FIGS. 1 and 2 is provided with a dry chemical reagent consisting of 1kU GDH, glucose dehydrogenase

220 U NAD 0.3 mmol MTT 250 g White Saponin®

50 mg Pluronic P85®

250 μl. water subjected to ion-exchange

The components of the reagent are finely divided into a suspension and can be coated onto the cuvette walls by different printing techniques, such as silk screen printing, cylinder printing, etc. In certain cases, surface-tension reducing substances may be added for facilitating the coating of hydrophobic plastic materials. In order to adapt this suspension to different coating equipment, the viscosity can be varied by adding suitable high-molecular weight polymers. The choice of high-molecular weight polymers is not critical, but the choice will affect the dissolution rate of the dry reagent. Suitable polymers include polyethylene glycol, polyvinyl pyrrolidone, dextran and different cellulose derivatives. The choice of polymer can also be made with a view to stabilizing the suspension. The reagent can be adapted to different surfaces based on known preparation techniques in the foodstuffs or cosmetics industry.

The glucose reagent is provided in cavity 16. Cavity 16 filled with whole blood, initiating reaction with the glucose reagent which converts glucose into a photometrically measurable color and end-point after about 3 minutes. The transfer into the cavity 22 can be effected after the red blood cells have been ruptured, which is about 1 minute after the reaction commences. In the same way as in the case of hemoglobin, photometering is carried out in a low-turbid, clear, aqueous solution. The distance between the walls in the cavity 21 is about 0.14 mm for glucose determination in whole blood. The photometric method for determining glucose and hemoglobin in whole blood is advantageously performed by a two-wavelength measurement.

EXAMPLE 2

Determination of glucose and protein in serum or plasma

When determining an analyte in plasma or serum, the red blood cells, the erythrocytes, should be excluded. The cuvette according to FIG. 7 is particularly well suited for analyzing in plasma or serum when the cuvette has several cavities and the communication between the different cavities is maintained by centrifugal force. Blood is drawn into a cavity by capillary force after direct sampling, and plasma or serum is transferred during centrifugation of the cuvette by centrifugal force into a cavity containing a reagent composition, specifically suited for determining the analyte.

Glucose in plasma or serum

The cuvette of FIG. 7 is provided with the following reagent composition:

Reagent composition, 1 ml:

1 Ku GDH, glucose dehydrogenase enzyme

220 U NAD 0.3 mmol MTT 50 mg Pluronic P85

250 µl. water subjected to ion-exchange

The reagent chemicals included are coated upon the cuvette as in the previous example of determining glucose in whole blood. Any modification of the reagent composition to achieve a dry reagent and adhesion to the walls of the cuvette cavity is in accordance with the description in the previous Example.

The reagent composition described above is applied in the cavity 22 such as by printing technique uniformly over the surface thereof. A lid is placed over cavities and other channels in the structure. Whole blood is sampled and flows into the cavity 16 by capillary action. After sampling, the cuvette is centrifuged. The heavier red blood cells settle in lower section 22b of cavity 22, while plasma is retained in upper section 22a as a result of capillary action. The reagent composition dissolves in serum or plasma, and the chemical reaction permits a specific determination of glucose. The chemical reaction, i.e. the glucose content, can be read directly in the cuvette by photometric technique.

Protein in serum or plasma

A suitable reagent composition consists of:

1 mmol lithium tartrate 1 mmol copper tartrate 7 mmol lithium hydroxide

These chemical substances are dissolved in water. The solution is evaporated so that the remaining portion which is applied will have the proper viscosity for application in the cavity by printing technique. Application by printing technique is facilitated if the dry reagent additionally contains about 0.5–2% lithium lauryl sulphate and about 1–5% polyvinyl pyrrolidone/polyvinyl acetate copolymer and optionally, a plasticizer.

The reagent is applied in the cavity 22 in a cuvette according to FIGS. 1 and 2. The cuvette functions in the same manner as the cuvette used for glucose determination is plasma or serum.

The cuvette according to the invention can be used for many types of analyses and is especially well suited for routine blood analyses, such as determination of glucose, urea-nitrogen in blood, albumin, bilirubin, and total protein, particularly on the basis of whole blood.

We claim:

1. A cuvette comprising:
   a) at least one first cavity having an inlet arranged to take up a liquid sample by capillary action;
   b) at least one second cavity for receiving liquid from said at least first cavity and;
   c) at least one channel in communication with said at least one first cavity and said at least one second cavity for transporting liquid from a) to b) only upon the application of centrifugal force upon the cuvette, the at least one channel having a depth that is greater than the depth of the first cavity.

2. The cuvette as set forth in claim 1 wherein the cuvette is provided in the at least one channel with a hydrophobic filter.

3. The cuvette as set forth in claim 1 wherein at least one reagent is located in at least one of the at least one first cavity or the at least one second cavity.

4. The cuvette as set forth in claim 1 wherein the at least one second cavity comprises a first section in fluid communication with a second section, the first section is adjacent to the at least one channel and the second section having a depth relatively greater than the first section which is constructed and arranged to exert a capillary action.

5. The cuvette as set forth in claim 1 wherein the at least one second cavity comprises a plurality of second cavities and the at least one channel comprises a plurality of channels, and each of the second cavities is in fluid communication with a respective channel exerting a liquid transporting function operative only upon the application of an centrifugal force upon the cuvette, each of the channels being in fluid communication with the at least one first cavity.

6. The cuvette as set forth in claim 1 wherein said at least one first cavity comprises a plurality of first cavities, said at least one second cavity is a single second cavity and said at least one channel comprises a plurality of first channels, each of the first cavities in fluid communication with a respective first channel, and each of the first channels in fluid communication with the single second cavity, the single second cavity being in fluid communication with a second channel which is in fluid communication with a third cavity.

7. The cuvette as set forth in claim 6 wherein at least one of the plurality of first cavities is provided with a seal and means for perforating the seal upon the application of centrifugal force upon the cuvette.

8. The cuvette as set forth in claim 1 wherein at least a portion of the cuvette is provided with a semi-permeable membrane.

* * * * *